United States Patent

Hardy et al.

[11] 4,051,249
[45] * Sept. 27, 1977

[54] SALTS OF 2-ALKYLTHIAZOLE-5-METHANOL DERIVATIVES

[75] Inventors: Michel Hardy, Maisons-Alfort; Daniel Humbert, Paris, both of France

[73] Assignee: Roussel-UCLAF, Paris, France

[ * ] Notice: The portion of the term of this patent subsequent to May 18, 1993, has been disclaimed.

[21] Appl. No.: 650,291

[22] Filed: Jan. 19, 1976

[30] Foreign Application Priority Data

Jan. 22, 1975   France ............................ 75.01972

[51] Int. Cl.² ..................................... C07D 277/24
[52] U.S. Cl. ........................... 424/270; 260/302 R; 424/200
[58] Field of Search ................................ 260/302 R

[56] References Cited

U.S. PATENT DOCUMENTS 3,957,809   5/1976   Hardy et al. .................. 260/302 R Primary Examiner—Richard J. Gallagher
Attorney, Agent, or Firm—Hammond & Littell

[57] ABSTRACT

Non-toxic, pharmaceutically acceptable acid addition salts of a compound of the formula

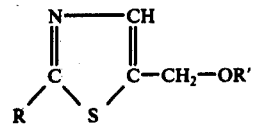

wherein R is an alkyl of 2 to 12 carbon atoms and R' is selected from the group consisting of hydrogen, alkyl of 1 to 8 carbon atoms and acyl of an organic carboxylic acid of 1 to 12 carbon atoms having antilipolytic activity and a very prolonged vasodilatatory activity.

9 Claims, No Drawings

SALTS OF 2-ALKYLTHIAZOLE-5-METHANOL DERIVATIVES

STATE OF THE ART

Zubarovskii et al. [Chem. Ab., Vol. 58 (1963), p. 2525b] describes the preparation of 2-methyl-thiazole-5-methanol by reaction of ethyl 2-methyl-thiazole-5-carboxylate with lithium aluminum hydride but does not describe any pharmacological properties therefor.

Our copending commonly assigned U.S. Patent application Ser. No. 495,556 filed Aug. 8, 1974, now U.S. Pat. No. 3,957,809, describes novel thiazole derivatives of the formula

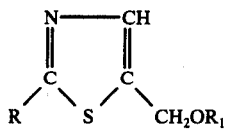

I wherein R is alkyl of 2 to 12 carbon atoms and $R_1$ is selected from the group consisting of hydrogen, alkyl of 1 to 8 carbon atoms and acyl of an organic carboxylic acid of 1 to 12 carbon atoms having hypolipemiant activity with a very prolonged vasodilatatory activity and their preparation.

OBJECTS OF THE INVENTION

It is an object of the invention to provide the novel thiazole derivatives of formula I and a process for their preparation.

It is another object of the invention to provide novel hypolipemiant and vasodilatatory compositions.

It is a further object of the invention to provide a novel method of inducing hypolipemic and vasodilatatory activity in warm-blooded animals.

These and other objects and advantages of the invention will become obvious from the following detailed description.

THE INVENTION

The novel thiazole derivatives of the invention are the non-toxic, pharmaceutically acceptable acid addition salts of compounds of the formula

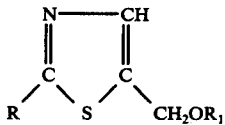

I wherein R is alkyl of 2 to 12 carbon atoms, and $R_1$ is selected from the group consisting of hydrogen, alkyl of 1 to 8 carbon atoms and acyl of an organic carboxylic acid of 1 to 12 carbon atoms.

Among the preferred compounds of formula I are those where R is a linear alkyl such as ethyl, n-propyl, n-butyl, n-pentyl, n-hexyl or n-undecyl; and $R_1$ is hydrogen, alkyl of 1 to 4 carbon atoms such as methyl, ethyl, propyl, isopropyl, butyl, isobutyl or tert.-butyl or acyl of a saturated or unsaturated aliphatic acid, particularly alkanoic acids such as formic acid, acetic acid, propionic acid, butyric acid, isobutyric acid or undecylic acid; cycloalkylcarboxylic acids or cycloalkylalkanoic acids such as cyclopropylcarboxylic acid, cyclopentylcarboxylic acid, cyclohexylcarboxylic acid, cyclopentylacetic acid, cyclohexylacetic acid, cyclopentylpropionic acid or cyclohexylpropionic acid; benzoic acid or phenylakanoic acids such as phenylacetic acid or phenylpropionic acid.

The most preferred basic compounds for the formation of the acid addition salts of the invention are 2-ethyl-thiazole-5-methanol, 2-propyl-thiazole-5-methanol and 2-hexyl-thiazole-5-methanol.

The novel process of the invention for the preparation of compounds of formula I in which $R_1$ is hydrogen comprises reacting a compound of the formula

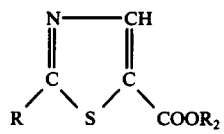

II wherein R has the above definition and $R_2$ is hydrogen or alkyl of 1 to 8 carbon atoms with a reducing agent to form the corresponding compound of formula I in which $R_1$ is hydrogen. The latter may be reacted with an etherification agent or an esterification agent to form the compounds of formula I wherein $R_1$ is alkyl of 1 to 8 carbon atoms or acyl of an organic carboxylic acid of 1 to 12 carbon atoms. The resulting compound of formula I is then reacted with an acid preferably in an organic solvent such as ethyl acetate, chloroform or methylene chloride.

Preferably, $R_2$ is alkyl of 1 to 4 carbon atoms. The reuducing agent is preferably a mixed hydride such as lithium aluminum hydride or lithium borohydride. The reduction may also be effected with sodium in the presence of an alkanol such as methanol or ethanol. The reduction may be effected in one or more organic solvents, preferably an ether such as dioxane, ethyl ether or tetrahydrofuran. The preferred mode of the invention comprises using lithium aluminum hydride in tetrahydrofuran.

The etherification reaction is preferably effected with an alkyl halide such as an alkyl iodide or chloride in the presence of a basic agent such as sodium or sodium hydride. The reaction may also be effected by reacting alkyl sulfates, sulfonates or sulfites with alkali metal alcoholates of the compounds of formula I wherein $R_1$ is hydrogen. The reaction may also be a dehydration of the alcohol of formula I with an alcohol in the presence of sulfuric acid.

The esterification of the alcohols of formula I is preferably obtained by reaction with the acid or a functional derivative thereof such as the acid anhydride or an acid halide, preferably the acid chloride or bromide.

The starting compounds of formula II may be prepared by the process described in French Pat. No. 2,047,876.

The acid addition salts are preferably derived from a strong acid. Examples of suitable acid to form the said salts are mineral acids such as hydrochloric acid, hydrobromic acid, hydroiodic acid, nitric acid, sulfuric acid, phosphoric acid, etc. and organic acids such as alkyl monosulfonic acids like methane sulfonic acid, ethane sulfonic acid and propane sulfonic acids, alkyldisulfonic acids like methane disulfonic acid, α,β-ethane disulfonic acid and α,β-propane disulfonic acid and arylmonosulfonic acids and aryldisulfonic acids such as benzene sulfonic acid.

Among the preferred salts of the invention are those of a strong acid and a compound of formula I wherein R' is hydrogen. Most preferred are the non-toxic, pharmaceutically acceptable strong acid addition salts, particularly of 2-ethylthiazole-5-methanol, and particularly α,β-ethane disulfonate of 2-ethyl-thiazole-5-methanol.

The novel hypolipemiant and vasodilatatory compositions of the invention are comprised of an effective amount of at least one non-toxic, pharmaceutically acceptable acid addition salt of a thiazole of formula I and a pharmaceutical carrier. The concentration of the active ingredient may be 5 to 95%, preferably 10 to 50%, by weight of the composition. The composition may be in the form of tablets, coated tablets, cachets, capsules, granules, emulsions, drops, syrups, suppositories or injectable solutions or suspensions.

The compositions have a marked antilipolytic activity and a very prolonged vasodilatatory activity and therefore are useful for the treatment of acute or chronic hyperlipidemia, of coronary insufficiencies, cardiac insufficiencies of atheromatosis origin, of chronic anginic states and of functional troubles of hypertension.

The novel acid addition salts of the invention have a certain number of advantages over the free bases of formula I. The compounds of the invention are solids which can be isolated in their crystalline form and are water soluble while the free bases of formula I are generally liquids which are only slightly water soluble. This means the salts of the invention are easier to purify and to put into solutions which presents therapeutic and industrial advantages.

In the case of medicaments, it is preferred to dispense a solid active principle when preparing it in the pharmaceutical form. For example, it is much more difficult to prepare a tablet containing a liquid active principle because there is needed to include in the tablet several excipients, in large proportions, which increases the weight and size of the tablet. Moreover, the injectable solutions are more difficult to prepare with the free bases of formula I which are slightly water soluble liquids and this requires the use of non-aqueous solvents which leads to injectable forms which can not be therapeutically used as easily as injectable aqueous solutions.

The active principle can be incorporated in the usual excipients for pharmaceutical compositions such as talc, arabic gum, lactose, starch, magnesium stearate, cacao butter, aqueous or non-aqueous vehicles, fatty bodies of animal or vegetable origin, paraffinic derivatives, glycols, diverse wetting agents, dispersants or emulsifiers or preservatives.

The novel method of the invention for inducing hypolipemic and vasolidatatory activity in warm-blooded animals comprises administering to warm-blooded animals, including humans, an effective amount of at least one non-toxic, pharmaceutically acceptable acid addition salt of a thiazole of formula I. The product may be administered orally, rectally or transcutaneously. The usual daily dose is 2 to 50 mg/kg.

In the following examples there are described several preferred embodiments to illustrate the invention. However, it should be understood that the invention is not intended to be limited to the specific embodiments.

EXAMPLE 1

α,β-ethane disulfonate of 2-ethyl-thiazole-5-methanol

STEP A: methyl 2-ethyl-thiazole-5-carboxylate

A solution of diazomethane in methylene chloride was added to a suspension of 10.45g of 2-ethyl-thiazole-5-carboxylic acid in 30 ml of methylene chloride until efferversence stopped and the methylene chloride was distilled The oily residue was chromatographed over silica and was eluted with a 1:1 mixture of benzene-ethyl acetate to obtain 11.3 g of methyl 2-ethyl-thiazole-5-carboxylate.

STEP B: 2-ethyl-thiazole-5-methanol 2.4 g of mixed lithium aluminum hydride was added under nitrogen to a solution of 11.3 g of methyl 2-ethyl-thiazole-5-carboxylate in 100 ml of anhydrous tetrahydrofuran at 20 to 25° C and the mixture was refluxed for 1 ½ hours. After cooling the mixture, excess lithium aluminum hydride was destroyed by the addition of ethyl acetate. The mixture was added to water and was vacuum filtered. The recovered precipitate was empasted with ethyl acetate and then with a methanol-methylene chlorine mixture. The filtrate was washed with water, dried and evaporated to dryness to obtan 9.5 g of an oil which was rectified under reduced pressure to obtain 8.9 g of 2-ethyl-thiazole-5-methanol with a boiling point of 78° C at 0.1 mm Hg.

STEP C: α,β-ethane disulfonate of 2-ethyl-thiazole-5-methanol

A solution saturated with ethane disulfonic acid in ethyl acetate was added to a mixture of 2.020 g of 2-ethylthiazole-5-methanol and 10 ml of ethyl acetate until the pH was about 2.5 and the mixture was vacuum filtered. The recovered precipitate was washed with ethyl acetate and dried to obtain 3.4g of product which was crystallized from isopropanol to obtain 3 g of α,β-ethane disulfonate of 2-ethyl-thiazole-5-methanol melting at 136° C.

Analysis: $C_7H_{12}No_4S_2$: Calculated: %C, 35.28; %H, 5.07; %N, 5.87; %S, 26.91. Found: %C, 35.2 %H, 5.1; %N, 5.6; %S, 27.1.

EXAMPLE 2

Tablets were prepared from 50 mg of the product of Example 1 and sufficient excipient of lactose, talc, starch and magnesium stearate to form 500 mg tablets.

PHARMACOLOGICAL DATA

A. Acute toxicity

The acute toxicity of α,β-ethane disulfonate of 2-ethyl-thiazole-5-methanol was determined on groups of 10 mice weighing between 18 to 22 g and the product was administered intraperitoneally as a suspension in carboxymethylcellulose. The animals were observed for one week and the average lethal dose ($DL_{50}$) was found to be about 550 mg/kg.

B. Antilipolytic activity

Male rats of the Sprague Dawley SPF strain weighing about 180 to 200 g were starved for 24 hours and then were given the product of Example 1 orally. One hour after the oral administration, the animals were killed by carotidienne section and samples of the blood were obtained to determine the dosage of free fatty acids. The extraction of the free fatty acids was made by the technique of Dole [J. Clin. Invest., Vol, 38 (1959), p. 1544–1544] as modified by Trout et. al. [J. Lipid, Res., Vol. 1 (1960) p. 199–202]. The plasmatic extract free of phospholipids was colorimetrically determined by the method of Anthonis [J. Lipid. Res., Vol. 6 (1965), p. 307–312]. Under these test conditions, the dose of α,β-ethane disulfonate of 2-ethyl-thiazole-5-methanol which reduced by 50% the level of free fatty acids in the treated animals as compared to the controls ($DA_{50}$) was found to be 2.5 mg/kg.

C. Cutaneous vasodilatatory effect

The cutaneous vasodilatory effect was determined on albino guinea-pigs and was manifested by the appearance of a reddening of the ears after a certain latency time. The animals were not fed and the product of Example 1 was orally administered. The time for the reddening appearance of the ears and the duration and intensity was noted on a subjective scale of 1 to 3. At a dose of 20 mg/kg, the latency period was 19 minutes for a duration of 61 minutes and an intensity of 2.3. The vasodilatatory activity was manifested at much higher doses than the antilipolytic activity and it did not appear until after a fairly considerable latency time.

Various modifications of the products and methods of the invention may be made without departing from the spirit or scope thereof and it is to be understood that the invention is intended to be limited only as defined in the appended claims.

We claim:

1. The non-toxic, pharmaceutically acceptable acid addition salts of a compound of the formula

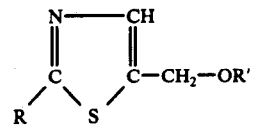

wherein R is an alkyl of 2 to 12 carbon atoms and R' is selected from the group consisting of hydrogen, alkyl of 1 to 8 carbon atoms and acyl of an organic carboxylic acid of 1 to 12 carbon atoms selected from the group consisting of alkanoic acids, cycloalkylcarboxylic acids, cycloalkylalkanoic acids, benzoic acid and phenylalkanoic acids.

2. The salt of claim 1 wherein R' is hydrogen.

3. A salt of claim 1 of 2-ethyl-thiazole-5-methanol.

4. The salt of claim 3 wherein the acid is $\alpha,\beta$-ethane disulfonic acid.

5. An hypolipemiant and vasodilatatory composition comprising an hypolipemiantly and vasodialatatorily effective amount of at least one acid addition salt of claim 1 and an inert pharmaceutical carrier.

6. A composition of claim 5 wherein the said salt is the $\alpha,\beta$-ethane disulfonate of 2-ethyl-thiazole-5-methanol.

7. A method of inducing hypolipemic and vasodilatatory activity in warm-blooded animals comprising administering to warm-blooded animals an hypolipemically and vasodilatatorily effective amount of at least one salt of claim 1.

8. The method of claim 7 wherein the salt is derived from 2-ethylthiazole-5-methanol.

9. The method of claim 8 wherein the acid is $\alpha,\beta$-ethane disulfonic acid.

* * * * *